United States Patent [19]

Thomas et al.

[11] 4,165,359
[45] Aug. 21, 1979

[54] AUTOCLAVE ASEPTOR

[75] Inventors: Michael D. Thomas, Elmhurst; Francis E. Ryder, Barrington, both of Ill.

[73] Assignee: Ryder International Corporation, Schaumburg, Ill.

[21] Appl. No.: 637,514

[22] Filed: Dec. 4, 1975

[51] Int. Cl.² .............................................. A61L 3/00
[52] U.S. Cl. ......................................... 422/105; 49/2; 70/DIG. 10; 219/415; 219/419; 219/433; 219/521; 292/DIG. 66; 422/300
[58] Field of Search .................... 21/85, 86, 89, 92, 94, 21/99, 119; 49/2; 292/DIG. 66; 70/DIG. 10; 219/415, 433, 521, 419

[56] References Cited

U.S. PATENT DOCUMENTS

| 1,326,124 | 12/1919 | Vischer, Jr. | 292/DIG. 66 |
|---|---|---|---|
| 2,277,605 | 3/1942 | Palitzsch | 219/521 |
| 2,500,241 | 3/1950 | Brown | 21/89 |
| 2,598,067 | 5/1952 | O'Brien | 292/DIG. 66 |
| 3,116,398 | 12/1963 | Welch | 292/DIG. 66 |
| 3,725,972 | 4/1973 | McCabe | 49/2 X |
| 3,801,278 | 4/1974 | Wagner et al. | 21/86 |

FOREIGN PATENT DOCUMENTS 105578 12/1966 United Kingdom ..................... 219/521

Primary Examiner—Arnold Turk
Attorney, Agent, or Firm—Trexler, Wolters, Bushnell & Fosse, Ltd.

[57] ABSTRACT

A sterilizer or aseptor for contact lenses and the like is disclosed, which provides a capsule adapted to both carry and sterilize a single set of contact lenses. The sterilizer includes a well adapted to receive the capsule, and when the well is heated, sterilizing action occurs within the capsule. A cover is locked into a closed position to prohibit access to the capsule and well when the well is heated to an elevated temperature.

1 Claim, 7 Drawing Figures

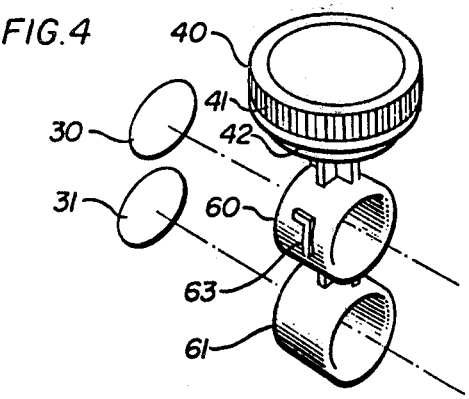
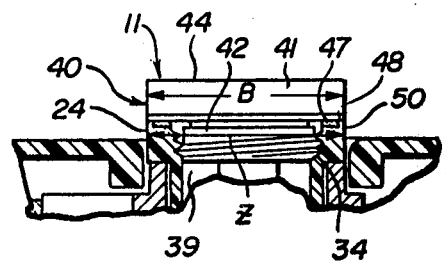
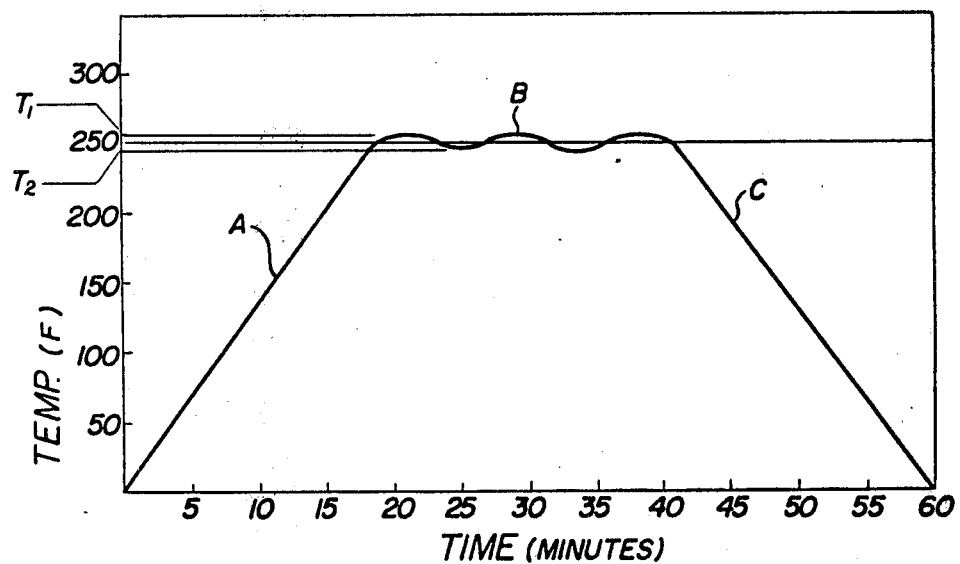
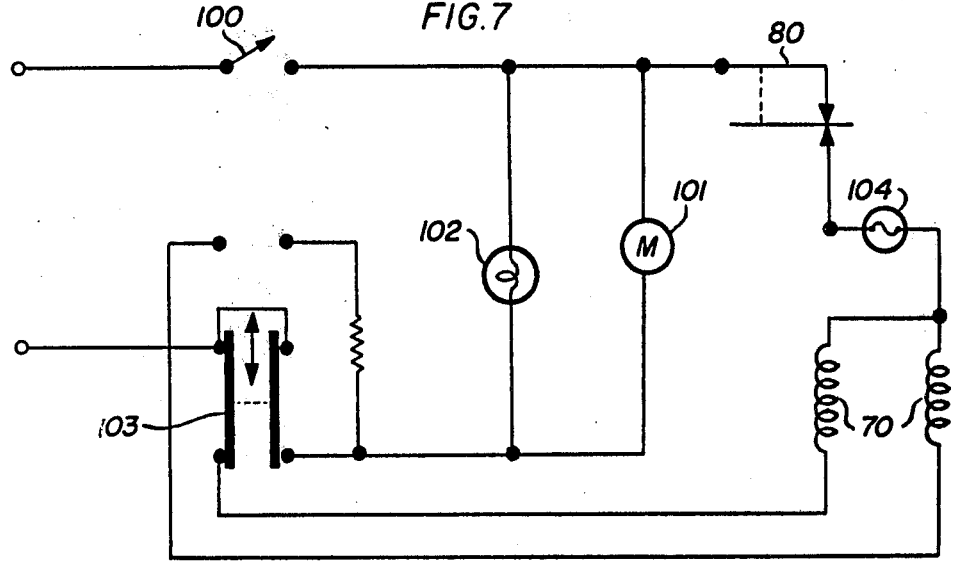

AUTOCLAVE ASEPTOR

BACKGROUND OF THE INVENTION

The present invention relates to aseptors for small objects such as contact lenses and the like.

Hydrophilic contact lenses, sometimes called soft contact lenses, are water absorbent, and must be periodically sterilized or asepticized. This sterilization can be effected by heating the lenses in an aqueous saline solution before use.

A number of contact lens sterilizers have been offered to accomplish this task, but for the most part these are of the boiler type. That is they employ a boiler in which distilled water is placed, the capsule containing the contact lenses being disposed in said water. The distilled water is brought to a boil and acts as the medium for transferring heat to the capsule containing the lenses and the sterilizing solution. Several disadvantages or limitations are inherent in this type of unit. First, the sterilizing temperature is generally limited to that of the boiling point of the water in the boiler unit, i.e. approximately 212° F. Secondly, units of this type generally employ the water as a timing media; that is, once the water boils away an over heat thermostat will de-energize the heater when the unit temperature exceeds 212° F. Accordingly, the period of time for which sterilizing temperatures can be maintained, is limited by the liquid capacity of the unit. For this reason, many of these sterilizers are quire large, and ill-suited for their intended use. In addition, some lens sterilizers require following a multistep procedure which, even in its most simplified form, may not be self-evident to an inexperienced user. Other sterilizers require specialized vials or holders to mount the lenses for sterilization. Still others such as the above-mentioned boiler, use a runaway thermostat and related apparatus wherein the heat conducting water is completely boiled away or otherwise evaporated, a sterilizing container temperature rises, and a thermostat then disconnects a heating element. Such arrangements generate unnecessary heat and consume unnecessary power, in contrast to the present invention.

Accordingly, it is the general object of the present invention to provide an autoclave aseptor or sterilizer and associated capsule designed so that the capsule can be used for both sterilizing the lenses and for securely carrying them in a handy manner. Obversely, it is an object to provide an aspetor device in which hot liquid and vapor is contained only within a compact capsule, permitting attainment of sterilizing temperatures in excess of the normal boiling point of the sterilizing solution.

A more specific object is to provide a capsule especially adapted for use with an autoclave, the capsule being designed to securely hold the lenses in a liquid- and vapor-tight chamber to permit the lenses to be carried and to be sterilized without loss of fluid.

It is another object of the invention to provide an autoclave especially adapted for home or ultimate consumer use. A related object is to provide such an autoclave which is designed for effective use with but a single set of lenses.

Yet another object is to provide such an autoclave having enhanced safety features which minimizes the user's opportunity for burning or otherwise injuring himself. A correlative object is to provide such an autoclave which automatically locks the novel capsule within a housing arrangement during heating and sterilizing.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 4 is an exploded view showing in still further detail part of the capsule structure and related contact lenses to be sterilized;

FIG. 5 is a partial sectional view of the top of the lens capsule;

FIG. 6 is a chart showing in somewhat schematic form the heating and sterilizing cycle of the autoclave and associated capsule by defining typical heat well and capsule temperature as a function of time; and FIG. 7 is a schematic diagram of the electrical circuitry used in this novel device.

DETAILED DESCRIPTION

Figures 1, 2, 3:
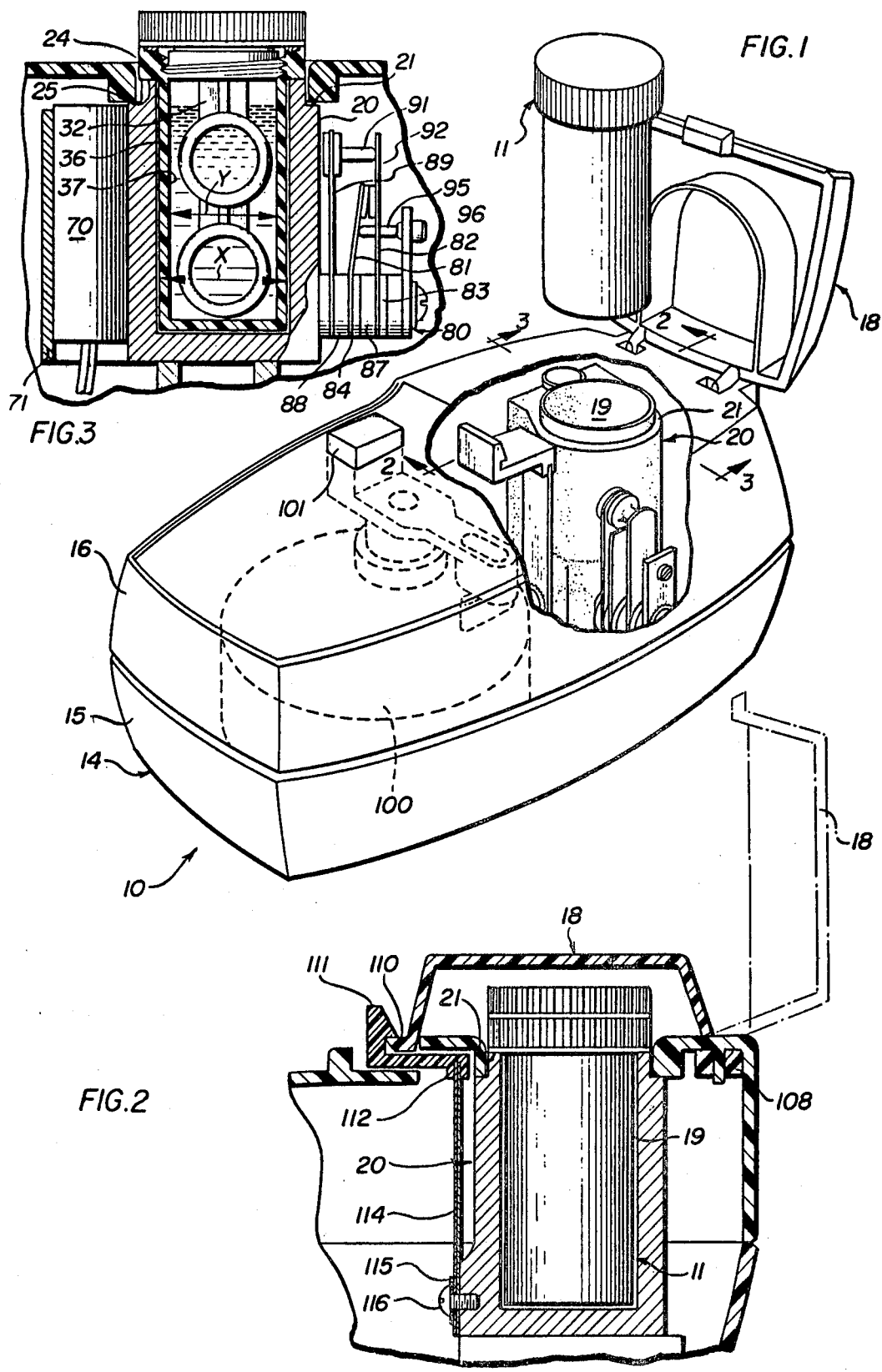
FIG. 1 is a perspective view showing the aseptor autoclave and associated capsule in their general aspects.
FIG. 2 is a fragmentary sectional view taken substantially in the plane of line 2—2 in FIG. 1 showing in further detail the capsule, the self-locking structure of the autoclave, and associated apparatus.
FIG. 3 is a sectional view taken substantially in the plane of line 3—3 in FIG. 1 and showing in further detail the capsule and its heater.

While the invention will be described in connection with a preferred embodiment, it will be understood that it is not intended to limit the invention to this embodiment. On the contrary, it is intended to cover all alternatives, modifications and equivalents as may be included within the spirit and scope of the invention.

Turning first to FIGS. 1-3, there is shown the novel autoclave 10 and capsule 11 of the present invention. To the ultimate user, this autoclave 10 presents a housing 14, which may for convenience be formed in two abuttive parts 15 and 16. Upon pivoting a cover 18 to an open position, (see FIGS. 2 and 3), the capsule 11 is revealed; when the capsule 11 is removed, the interior 19 of a heating well 20 and an annular well top 21 can be seen.

To provide a handy carrying case which can also and alternatively be used for sterilizing the contact lenses in accordance with the invention, the capsule 11 comprises a right cylindrical body portion 23 formed to a predetermined outer diameter X and inner diameter Y. A capsule mouth 24 has an enlarged outer diameter Z; this difference between the enlarged mouth outer diameter Z and body outer diameter X defines an annular shoulder 25 which is adapted to support the capsule 11 on and in the supporting autoclave heat well structure 20.

To assure easy insertion and removal of contact lenses 30, 31 and lens supporting mast 32 (see FIG. 4), female threads 34 are formed within the mouth 24 to a thread minor diameter at least as large as the capsule body inner diameter Y. An easily distinguishable fill line marking 36 is associated with a capsule body interior surface 37 as by engraving or embossing. When sterilizing liquid is added to the level of this marking 26, an amount of liquid is carried within the capsule which is sufficient to fully submerse the lenses 30, 31 and the carrying mast 32. However, a vapor accretive space 39 is provided above the liquid to permit boiling action and increased vapor pressure.

To enclose this capsule with a vapor-tight seal, a cap 40 includes a base 41 of a diameter B substantially equal to the mouth outer diameter Z so as to provide, when closed, the neat, uniform, unitary appearance illustrated in FIGS. 1 and 3. From the base 41, a pedestal 42 of reduced diameter depends; it is partly defined by male threads 44 adapted for mating engagement with the female threads 34, as shown in detail in FIG. 5. To retain a sealing ring 47 between the generally abuttive cap and mouth surfaces 48 and 49, the mouth surface 48 defines a ring-accepting annular groove 50. The male and female threads 34 and 44 are extended so as to permit the cap 40 to be screwed toward and into the body 23, thereby squeezing the sealing ring 47 with an interactive compression sufficient to retain the aqueous vapor under the pressure generated during sterilizing procedures. As will be appreciated from the above, due to the compression of seal 47 between cap 40 and the body 23, a sealed chamber is provided which precludes the escape of vapor. Accordingly, as the sterilizing solution is heated, vapor will accumulate in space 39, raising the internal pressure. Since the boiling point of a liquid is directly proportional to vapor pressures, with the autoclave unit of the design under discussion, it is possible to heat the sterilizing solution to a level well above the normal boiling point of the solution at atmospheric pressure. As will be discussed hereinafter, a sterilizing temperature of approximately 250° F. is desired.

As still an additional feature, the only liquid used in the sterilizing unit of the present invention is that contained within the capsule 11. Accordingly, unlike boiler type units as discussed above, there is no danger of spillage. Also, all vapor produced during heating is contained within the capsule 11, which is an advantage over boiler type units where steam vapor is allowed to escape, which can result in injury to the user or possible damage to furniture or the like.

In asepticizing lenses, it is important to mount the lenses securely, and yet to present the maximum lens surface area for direct contact with the sterilizing solution. To this end, as illustrated particularly in FIGS. 3 and 4, the lens mounting mast 32 projects from the pedestal 42. As illustrated particularly in FIG. 3, this mast 32 has only a maximum length sufficient to permit its complete insertion into the capsule body 23. Thus, complete enclosure of the mast 32 and any contained lenses 30, 31 can be accomplished within the capsule in a vapor-tight cap-body engagement.

As illustrated particularly in FIG. 4, the mast includes at least two annular rings 60 and 61 formed in and on the mast 32 for receiving and retaining the contact lenses 30, 31 by engagement with the lens edges. A distinguishing mark 63 (such as an embossed letter "L") is located in the vicinity of one lens ring 60 to distinguish that ring 60 and any lens 30 carried therein from the opposite ring 61 and its lens 31. Thus, left and right lenses can be readily distinguished from one another by even inexperienced users.

After the lenses 30 and 31 have been inserted into their rings 60 and 61 and the cap 40 attached to the body 23, the capsule 11 is inserted into the capsule-accommodating interior recess 19 formed in the thermally conductive well 20. To heat the well and capsule, an electric heating element 70 can be mechanically abutted against the well 20, as by a C-clamp 71 or other convenient structure. Thus, heat generated by the heater element 70 is conducted through the thermally conductive well 20 to the capsule 11, thereby causing the solution temperature to rise and aseptizing action to occur.

It is a feature of this invention that electrical energy is conserved, the maximum temperature reached in the autoclave is of a relatively low order, and no runaway thermostat arrangement is required. To this end, a thermostat device 80 is provided as shown in FIG. 3. Here, this thermostat 80 includes a relatively short electrical contact 81 located to face an extended contact 82; each contact is mated with an electrical lead 83 and 84. These contact and lead pairs 81-83 and 82-84 are insulated from one another and from other autoclave parts by electrical insulator 87 and 88. A bimetallic strip 89 in thermal communication with the well 20 is located near the extended contact 82. When the bimetallic strip 89 is heated, it is deformed and bends toward the contact 82 in well known manner. An electrically insulated contact point 91 engages the extended end 92 of the contact 82, and pushes the contact 82 away from its mating contact 81, thereby breaking the circuit. Adjustment of thermostat circuit breaking temperature is accomplished by an adjustment screw 95 mounted upon a pedestal 96. When the screw is axially reset, greater or less bimetallic strip motion will be required to break the contacts and de-energize the well heater circuit.

As can be seen from FIGS. 1 and 3, the heating element 70 is in conductive engagement with a surface portion of the well 20 at a first selected location. At a second selected location, and generally diametrically opposed to the heating element 70, there is mounted the thermostat 80 which is also in contact with the exterior surface of the well 20. Accordingly, the surface portion of the well 20 proximate said thermostat 80 will not be heated by the heating element 70 until such time as the interior well 19 has become totally and completely raised to the desired temperature. Thus, it is assured that the well 19 and the associated lens caps 11 will be heated to the desired sterilization temperature before the thermostat 80 is activated to de-energize the heater 70. As an additional matter, the bimetallic latch 114 is preferably located at a third exterior position with respect to the well 20, which position is intermediate the heater 70 and thermostat 80, such that the rate of heat transferred to the bimetallic latch 114 is greater than the rate of transfer to the thermostat 80. Thus, this arrangement assures that the bimetallic latch 14 is operated to lock the cover in a closed position at a safe temperature level, well before the sterilizing temperature sufficient to activate the thermostat is reached.

By means of appropriate circuitry schematically shown in FIG. 7, this thermostat and heater can be connected to a timer or starter unit 100 which may be any one of a number of known constructions. When an actuator switch 101 is operated, the heater 70 and the starter 100 are simultaneously energized. The temperature in the well 19 and the temperature of the encapsulated sterilizing solution can rise to a predetermined temperature such as, for example, a nominal 250°, as illustrated in FIG. 6 by the graph line A.

By appropriately setting the thermostat 80 as described above, the temperature can be maintained at a nominal 250°. A higher-than-maximum temperature $T_1$ causes deactivation of the thermostat 80 and deenergization of the heater 70. When the temperature of the heater 70, well 20 and thermally connected bimetallic strip 89 drop to a reactivating lower temperature $T_2$, the circuit is again closed and reheating begins. The result of this intermittent heater energization is only intermittent energy usage and a slightly oscillating capsule sterilizing temperature, as shown by the graph line B in FIG. 6. When a predetermined time, such as 40 minutes for example, has elapsed, the starter 100 irreversibly deenergizes the heating circuitry, causing the capsule temperature to again lower as illustrated by the graph line C in FIG. 6. An operating indicator light 102 and 120/240 line voltage selector switch 103 can be included for wide product appeal, and a fuse 104 is included for safety.

It is a feature of the invention that this device positively prohibits accidental removal of a heated capsule 11 from the autoclave device. In addition, the user is prohibited from accidentally burning or otherwise injuring himself during autoclave use. To this end, the lockable cover 18 is hinged by appropriate pivot structure 108 to the housing 14 for selective rotation between an open, capsule-access position and a closed position covering the capsule 11 and well 20. When the capsule 11 has been inserted into the well interior 19 in its sterilizing position, the capsule cover 18 is closed.

Mounted for sliding motion into and out of engagement with a cover lip 110 is a latch member 111. As illustrated particularly in FIG. 2, an interior end 112 of this latch member 111 is mounted upon a bimetallic strip 114 which is, in turn, secured at another end 115 to the well 20 in a thermally conductive position, as by a common screw 116 or other convenient device. By appropriate selection of bimetallic strip-constituent materials and bimetallic strip orientation, heat conducted from the well 20 to the bimetallic strip 114 will serve to displace the strip from the unlocked position shown in phantom lines shown in FIG. 2 to the locked position shown in solid lines. As a result of this bimetallic strip deformation, the latch 111 is drawn into positive locking engagement with the cover tip or lip 110, thereby positively locking the cover in a closed, access-prohibiting position when the well temperature exceeds a predetermined lock-activation temperature.

The temperature at which operation of the latch occurs is, as noted above, a function of the constituent material of the bimetallic strip 114, and this temperature is selected such that locking occurs at a sufficiently low temperature level to insure the prevention of injury to and the safety of the user.

The invention is claimed as follows:

1. An autoclave sterilizer for contact lenses, comprising in combination: a capsule of predetermined size and shape for housing said lenses and providing a vapor tight chamber in which said lenses and a sterilizing solution may be placed; a housing unit for receiving said capsule, said housing unit including; an exterior casing; a thermally conductive heat well structure disposed within said casing and including an interior well shaped to receive and to surround closely said capsule to maximize the transmission of heat from said heat well structure to said capsule; heater means for said heat well structure including a heating element engaged in an outer well structure wall portion at a first exterior location, said heating element being in abuting, heat transfer engagement with said heat well structure for the direct and conductive application of heat thereto; a thermostat device in operative engagement with said heat well structure at a second, exterior location to sense the temperature of said heat well structure at said location, said thermostat device being operatively associated with said heater means to deactivate same once a predetermined temperature is reached at said second exterior location, which predetermined temperature is in excess of the boiling temperature of the sterilizing solution to be placed in said capsule, when at atmospheric pressure; timing means for controlling the length of the sterilizing operation; a cover member pivotly connected to said casing for overlying said interior well and said capsule disposed therein; thermally activated latch means including a bimetallic strip having an end portion mounted in direct heat conductive engagement with said heat well structure at a third exterior location; a latch member carried by the opposite end of said bimetallic strip for selective mechanical engagement with said cover to latch said cover in place and preclude access to the interior well and capsule when said heat well structure is above a second predetermined, lock activating temperature which is lower than said first mentioned predetermined temperature and at a level to insure the safety of the user; said second location at which said thermostat device is mounted being disposed on an opposite side of said interior well with respect to said first location at which said heater element is in engagement with said well thereby insuring the heating of said well to the first mentioned predetermined temperature prior to the operation of said thermostat device to deactivate said heater means, and said third location at which said bimetallic strip is mounted, being intermediate said first and second locations to provide for the rapid transfer of heat to said bimetallic strip to insure the engagement of said latch to said cover prior to any portion of said heat well structure reaching said first predetermined temperature.

* * * * *